United States Patent
Sasajima et al.

(10) Patent No.: US 6,936,819 B2
(45) Date of Patent: Aug. 30, 2005

(54) MICROSTRUCTURED PATTERN INSPECTION METHOD

(75) Inventors: Fumihiro Sasajima, Hitachinaka (JP); Osamu Komuro, Hitachinaka (JP); Fumio Mizuno, Tokorozawa (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/857,956

(22) Filed: Jun. 2, 2004

(65) Prior Publication Data

US 2004/0217288 A1 Nov. 4, 2004

Related U.S. Application Data

(63) Continuation of application No. 10/389,882, filed on Mar. 18, 2003, now Pat. No. 6,765,204, which is a continuation of application No. 09/684,469, filed on Oct. 6, 2000, now Pat. No. 6,573,499.

(30) Foreign Application Priority Data

Oct. 7, 1999 (JP) .......................................... 11-287057

(51) Int. Cl.$^7$ ............................................. G01N 23/00
(52) U.S. Cl. ...................... 250/310; 250/306; 250/307; 250/491.1; 430/5
(58) Field of Search ................................ 250/287, 310, 250/306, 307, 491.1; 430/5

(56) References Cited

U.S. PATENT DOCUMENTS

| | | | |
|---|---|---|---|
| 4,855,253 A | 8/1989 | Weber | 437/8 |
| 5,412,209 A | 5/1995 | Otaka et al. | 250/310 |
| 5,412,210 A | 5/1995 | Todokoro et al. | |
| 5,512,746 A | 4/1996 | Saito | 250/310 |
| 6,232,787 B1 * | 5/2001 | Lo et al. | 324/751 |
| 6,426,501 B1 * | 7/2002 | Nakagawa | 250/310 |
| 6,509,750 B1 * | 1/2003 | Talbot et al. | 324/750 |

FOREIGN PATENT DOCUMENTS

JP 08-162383 6/1996

\* cited by examiner

*Primary Examiner*—Nikita Wells
*Assistant Examiner*—Zia R. Hashmi
(74) *Attorney, Agent, or Firm*—Kenyon & Kenyon

(57) ABSTRACT

The edges of the reticle are detected with respect to the microstructured patterns exposed by the stepper, and the shapes of the microstructured patterns at the surface and at the bottom of the photoresist are detected. The microstructured patterns are evaluated by calculating, and displaying on the screen, the dislocation vector that represents the relationship in position between the detected patterns on the surface and at the bottom of the photoresist. Furthermore, dislocation vectors between the microstructured patterns at multiple positions in a single-chip or single-shot area or on one wafer are likewise calculated, then the sizes and distribution status of the dislocation vectors at each such position are categorized as characteristic quantities, and the corresponding tendencies are analyzed. Thus, stepper or wafer abnormality is detected.

31 Claims, 14 Drawing Sheets

M1: CENTER OF THE INNER CIRCLE
M2: CENTER OF THE OUTER CIRCLE
V1: VECTOR OF DISLOCATION

A: CHARACTERISTICS FEATURES OF CIRCLES

1: TRUE CIRCLE    2: VERTICALLY LONG    3: HORIZONTALLY LONG    4: OBLIQUE (1)    5: OBLIQUE (2)

B: ELLIPTICITY

1: VERTICAL DIAMETER= HORIZONTAL DIAMETER    2: VERTICAL DIAMETER> HORIZONTAL DIAMETER    2: VERTICAL DIAMETER>> HORIZONTAL DIAMETER

C: AREA

1: LARGE    2: MEDIUM    3: SMALL (a)  (b)

(c)

(a)

(b)

(c)

(d)

A: SHAPE

1: PARALLEL     2: TAPERED DOWNWARD     3: TAPERED UPWARD

B: HORIZONTAL SIZE

1: STANDARD     2: LARGE     3: SMALL (a)

(b)                    (c)

| OWN ID | RECORD | PARENT ID | BROTHER ID | CHILD ID |
|---|---|---|---|---|
| 0 | .. | — | — | 1, 2 |
| 1 | .. | 0 | 2 | 3, 4 |
| 2 | .. | 0 | 1 | 5, 6 |
| 3 | .. | 1 | 4 | 7, 8 |
| 4 | .. | 1 | 3 | 9, 10 |
| 5 | .. | 2 | 6 | 11, 12 |
| 6 | .. | 2 | 5 | 13, 14 |
| 7 | .. | 3 | 8 | — |
| 8 | .. | 3 | 7 | — |

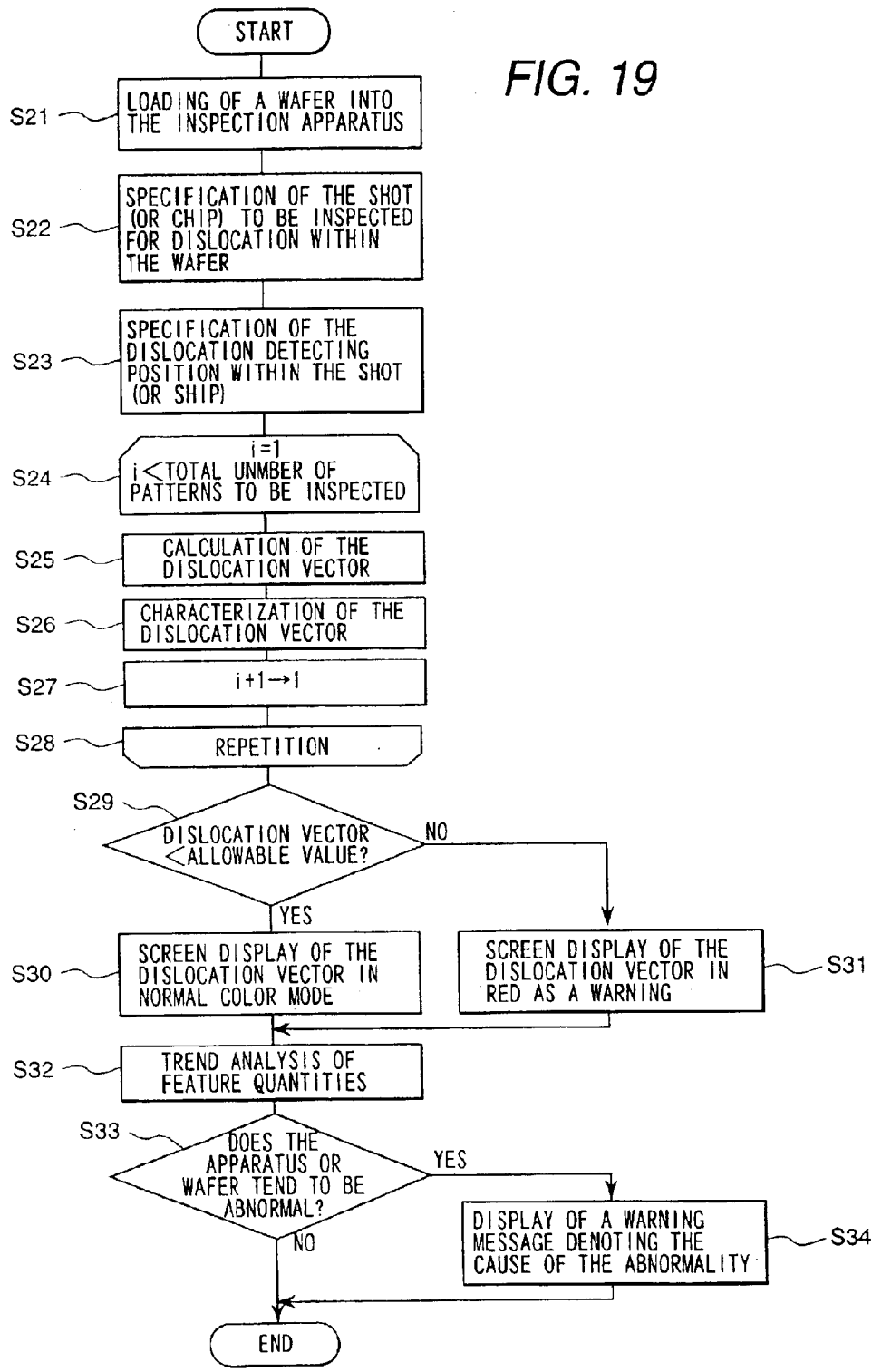

MICROSTRUCTURED PATTERN INSPECTION METHOD

CROSS REFERENCES TO RELATED APPLICATIONS

This is a continuation of application Ser. No. 10/389,882 filed Mar. 18, 2003, now U.S. Pat. No. 6,765,204 which is a continuation of application Ser. No. 09/684,469 filed Oct. 6, 2000, which issued as U.S. Pat. No. 6,573,499 on Jun. 3, 2003.

The present invention relates to microstructured pattern inspection method, particularly, to a method of inspecting the microstructured patterns, such as contact holes and linear patterns, that are formed on semiconductor wafers with the photolithography that uses an optical exposure apparatus such as a stepper.

In the manufacture of semiconductors, photolithography is used to form patterns on semiconductor wafers. The formation of these patterns most commonly uses the reduction projection alignment method that applies an apparatus in which a reticle formed by enlarging the circuit patterns for several chips is used for reduction projection alignment (hereinafter, this apparatus is referred to as the stepper). In the reduction projection alignment method using the stepper, a reduced image of the mask pattern of the reticle is exposed to light so as to be projected and formed on the photoresist coating of the wafer, with the result that a resist pattern, a copy of the reticle mask pattern, is formed on that wafer by processing chemically the photosensitized photoresist coating. The patterns for several chips that have been formed on the reticle can be copied with a single shot (exposure). This procedure is "stepped and repeated" to copy more such patterns on the wafer.

An example of forming contact holes on the insulating film of the wafer is described below. First, a photoresist coating is formed on the insulating film. Next, the photoresist coating undergoes exposure using a reticle provided with a pattern of contact holes of the design size and arrangement, and then undergoes chemical processing. After this, contact hole patterns passing through the insulating film can be formed on the wafer by performing processes such as etching, and in this etching process, the photoresist coating that has been created by copying the required pattern functions as a mask.

To ensure that the stepper forms patterns on the wafer as described above, the microstructured patterns on the dimensionally enlarged reticle must undergo reduction projection alignment on the wafer through projection optics. The surface and bottom of the exposed layer (photoresist coating) of the patterns that have been exposed to light in the reduction projection alignment process occasionally differ in size, shape, position, and other factors.

The first main cause of these differences is a combination of defects in the wafer material and defects in the workmanship of the substance exposed to light on the wafer, such as a resist. The warping, distortion, deflection, and the like, of the wafer itself can occur during its manufacture or according to the subsequent elapse of time or the particular ambient environmental conditions such as temperature, and these defects affect optical interference. The shapes of the patterns formed will also be affected by the nature of the substance to be used as a resist, and by the resist coating thickness, coating status, and other factors. Such deviations (from design specifications) in terms of the forming positions and dimensions at the exposed surface and bottom of the microstructured patterns due to the characteristics of the exposed substance (hereinafter, these deviations are collectively called "dislocations") are usually distributed over a wide range in a specific area of the wafer, and with a fixed tendency.

The second main cause is such insufficiency in the performance of the optics used in the stepper as schematized in FIG. 2. As shown in FIG. 2 (a), no problems occur in the vicinity of the reticle center. As shown in FIG. 2 (b), however, if light is emitted obliquely to the surface of the wafer, lens aberration, such as astigmatism or comatic aberration, will occur at the edges of the reticle. Dislocation due to such aberration mainly appears within a single-shot area, radially from its central position and with a fixed tendency.

The third main cause is a defect in the nature of the optics of the stepper, that is to say, a shift in focal position (defocusing), which arises from the fact that the lenses in the optics used for exposure suffer deformation due to the heat generated during exposure (this event is called "lens heating").

The fourth main cause is a defect in the performance of the optics of the stepper. If the optics of the stepper has any inclined parts such as lens, since the emitted light enters laterally, the exposure pattern within a single-shot area skews in a fixed direction.

Differences between the design specifications and actually formed patterns are mainly caused by the four factors described above. The first problem resulting from these differences is that dislocation occurs between the patterns that were formed on the surface and bottom of the photoresist. Similarly, there also occurs misalignment with respect to the pattern in the lower layer or upper layer of the insulator, due to the axial and position offsets between the design specifications and actually exposed patterns. Axial or position offsets in contact hole patterns reduce the area of the hole, thus increasing electrical resistance, and finally leading to deteriorated semiconductor performance. In some cases, the semiconductor loses electroconductivity, which is a critical defect in the semiconductor device itself.

With respect to these problems, at present, exposure accuracy at the bottom area of the microstructured patterns is usually evaluated by calculating the area of the bottom. However, there is no established method for evaluating quantitatively the optics of the stepper, the wafer, or the like, from the quantity or direction of pattern dislocation or from these factors.

SUMMARY OF THE INVENTION

The present invention is therefore intended to provide a method of evaluating each microstructured pattern of a semiconductor by calculating as a dislocation vector the relationship in position between the surface and bottom of the photoresist on the microstructured pattern. The present invention is also intended to provide a method of evaluating exposure accuracy quantitatively on a single-shot, single-chip, or wafer-by-wafer basis, or a method of evaluating each section of the pattern exposure system, detecting abnormality, and issuing a related warning.

During microstructured pattern evaluation based on the present invention, the formation status of the patterns on the surface of the exposed layer (hereinafter, simply called the surface layer) and at the bottom of the exposed layer (hereinafter, simply called the bottom layer) and the relationship in position between the surface layer and the bottom layer are analyzed, then the relative dislocation between both layers is calculated as a dislocation vector, and this vector is displayed on the screen of the corresponding apparatus. Also, a warning will be issued if the dislocation vector oversteps the dislocation tolerance that has been set beforehand. In addition, the exposure system, the wafer, and other targets can be evaluated by classifying calculated characteristic quantities according to the particular tendency and characterizing each single-shot, single-chip, or wafer area.

That is to say, according to the present invention, the microstructured pattern inspection method for inspecting the microstructured patterns formed on the thin coating of a substrate through pattern optical exposure is characterized in that said inspection method comprises a process for acquiring images of the microstructured patterns formed on said thin coating, a process for identifying both the shape of the microstructured pattern on the surface of said thin coating and the shape of the microstructured pattern at the bottom of said thin coating, from said images, and a process for detecting the dislocation between the two microstructured patterns that have been identified in the third process mentioned above. The shapes of the microstructured patterns can be identified by detecting the profiles of the patterns.

For circular microstructured patterns such as contact hole patterns, misalignment between the gravity center of the circular pattern on the surface of a thin coating and the gravity center of the circular pattern at the bottom of the thin coating is detected as a dislocation. For linear microstructured patterns, misalignment between the central axis of the linear pattern on the surface of said thin coating, and the central axis of the linear pattern at the bottom of said thin coating, is detected as said dislocation.

The dislocation of microstructured patterns can be visually and easily recognized by displaying at the patterns an arrow indicating the size and direction of the dislocation. It is desirable that the profiles of the microstructured patterns be displayed as marks such as approximate curves or discontinuous dots.

A microstructured pattern inspection method based on the present invention can further comprise a process in which said dislocation is detected at a plurality of positions within the required zone, and a process in which a dislocation that characterizes said zone is detected through statistical processing of the dislocation at said multiple positions. In this case, the dislocation of the entire microstructured patterns in the corresponding zone can be visually and easily recognized by displaying in that zone the appropriate arrow according to the particular size and direction of the dislocation characterizing the zone. This zone can be either a single-shot area or a single-chip area.

Since a process for comparing the distribution tendency of the dislocation at said multiple positions, and the distribution tendency of the dislocation estimated to occur if trouble is detected in the corresponding microstructured pattern forming apparatus, is also included in the microstructured pattern inspection method described above, trouble with the microstructured pattern forming apparatus can be detected.

In addition, according to the present invention, the microstructured pattern inspection method for inspecting the microstructured patterns formed on the thin coating of a substrate through pattern optical exposure is characterized in that said inspection method comprises a process for acquiring images of the microstructured patterns formed on said thin coating, a process for identifying the shapes of the microstructured patterns from said images, and a process for categorizing the corresponding microstructured patterns by the characteristic quantities of the respective shapes.

This microstructured pattern inspection method can also include a process in which the corresponding microstructured patterns are categorized at a plurality of positions within a single-shot or single-chip area, and a process in which the categories of the microstructured patterns characterizing said single-shot or single-chip area are determined through statistical processing of the categorizing results obtained at said multiple positions. During statistical processing of the categorizing results, the quantity of inspection within, for example, each shot or each chip, and the number of microstructured patterns belonging to a specific category are compared and the highest pattern in terms of rate is characterized as a typical pattern at the particular position. Overall characteristics can be visually and easily identified by displaying a single-shot or single-chip zone in the appropriate color according to the particular category of the microstructured patterns characterizing the corresponding single-shot or single-chip area.

Under the present invention, not only the edge positions corresponding to the surface and bottom of the exposed layers of the contact hole and/or linear patterns are displayed, but also the dislocation between the patterns on both layers is displayed as a dislocation vector at the same time. And a warning will be issued if the dislocation vector oversteps a predetermined tolerance. Thus, it becomes easy to automate the evaluation of microstructured pattern exposure accuracy and to confirm the exposure accuracy. In addition, not only the edge positions corresponding to the surface and bottom of the exposed layers of the contact hole and/or linear patterns are displayed, but also the characteristic quantities of exposed patterns in terms of shape are calculated at the same time. And a warning will be issued if these characteristic quantities overstep their tolerances. Thus, it becomes easy to automate the evaluation of microstructured pattern exposure accuracy and to confirm the exposure accuracy. In addition, it is valid to analyze the dislocation vector and characteristic quantities in combined form. Furthermore, useful data for trouble detection in the optics of the stepper, for statistical evaluation of thermal stresses due to thermal treatment over a wide range, and for statistical evaluation of lens aberration such as astigmatism or comatic aberration, can be collected by analyzing the distributions of the characteristic quantities of dislocation vectors and/or microstructured patterns over a broader area such as a single-chip or single-shot area or the entire wafer. And the inspection of said microstructured patterns to any multiple processes enables collected data to be fed back to subsequent processes.

BRIEF DESCRIPTION OF THE DRAWINGS

FIG. 19 is a flowchart explaining the entire procedure relating to a microstructured pattern inspection method based on the present invention.

DETAILED DESCRIPTION OF THE PREFERRED EMBODIMENTS

Embodiments of the present invention are described below with reference to the accompanying drawings. First, the methods of calculating and displaying the dislocation vectors with respect to the contact hole patterns and linear patterns formed on the exposed layer (photoresist coating) of the wafer are described. Next, the method of analyzing the causes of the dislocation by analyzing a multiplicity of dislocation vectors and deriving a general tendency is described.

Figure 1:
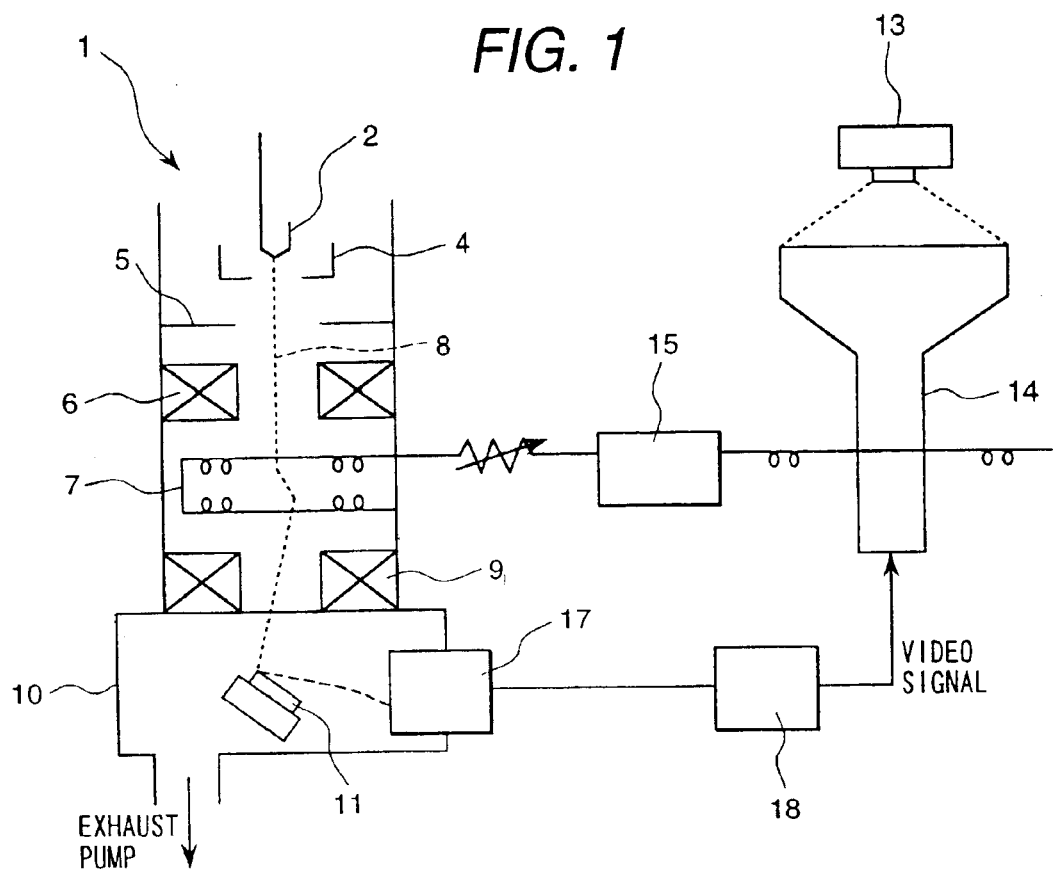
FIG. 1 is a schematic diagram showing an example of the microstructured inspection apparatus used for an inspection method based on the present invention.
Figure 2:
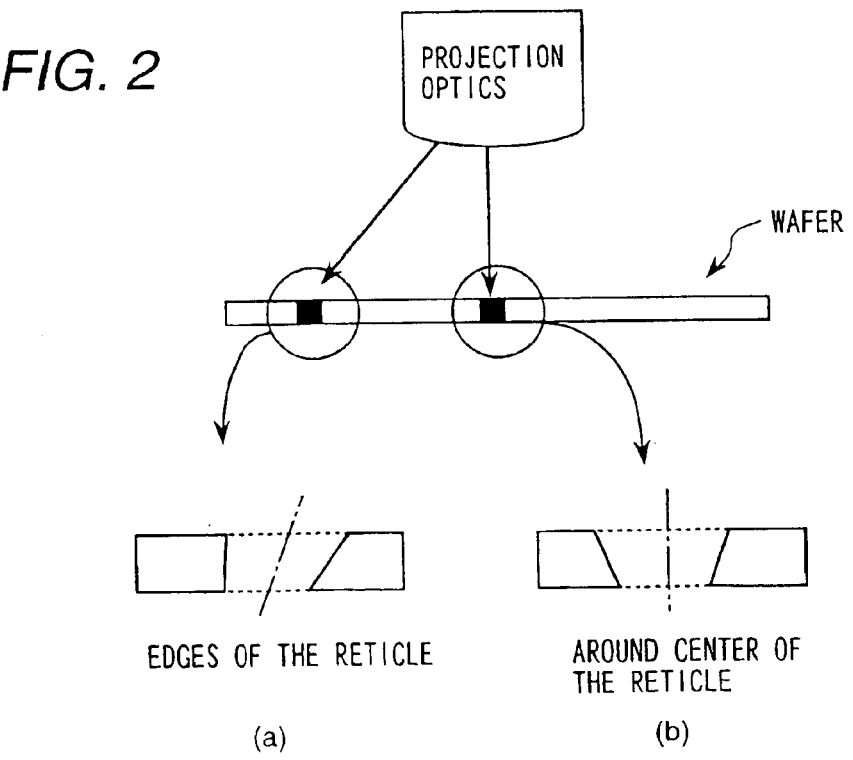
FIG. 2 is an explanatory diagram showing an example of abnormal exposure due to defects in the performance of the optics itself of the stepper.

FIG. 1 is a schematic diagram showing an example of a microstructured pattern inspection apparatus designed to be used for an inspection method based on the present invention. In FIG. 1, a scanning-type electronic microscope is shown as a typical microstructured pattern inspection apparatus. Electron gun 1 provides heating filament 2 with electroheating to obtain electron beam 8. Electron beam 8, after being drawn from Wehnelt units 4, is accelerated by anodes 5, then condensed through condensing lenses 6, and scanned by deflecting coil unit 7 to which deflecting signals are applied from deflecting signal generator 15. After that, object lenses 9 focus the electron beam on sample 11 placed in samples compartment 10. Thus, electron beam 8 is scanned one-dimensionally or two-dimensionally across sample 11 on which microstructured patterns are inscribed. When electron beam 8 is radiated, secondary electrons will be generated in the vicinity of the surface of sample 11 according to the particular shape of the sample and these electrons will be detected by secondary electron detector 17. The secondary electrons that have thus been detected will then be amplified by amplifier 18 to become the luminance modulated signals of CRT 14 synchronized with deflecting signal generator 15. The luminance modulated signals will reproduce the secondary electron images generated on the surface of sample 11 by the electron beam 8 that was radiated in synchronization. Information on the microstructured patterns formed on the surface of the sample can be acquired using this procedure.

The secondary electron images displayed on CRT 14 will be picked up by camera 13 as required.

Figure 3:
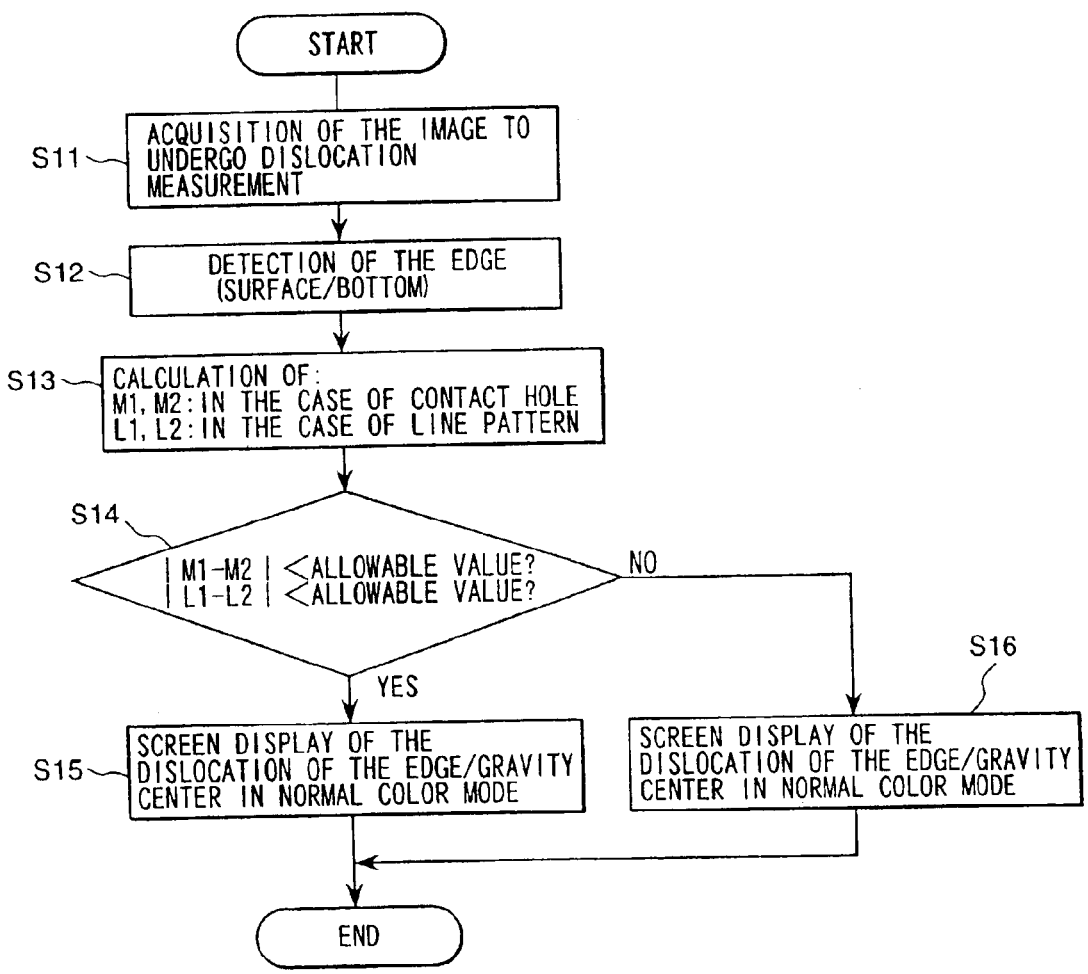
FIG. 3 is a flowchart of dislocation vector calculation.

FIG. 3 is a flowchart showing the flow of microstructured pattern dislocation vector calculation based on the microstructured pattern image information that has thus been acquired. The methods of detecting and displaying dislocation vectors in the case that the microstructured patterns to undergo dislocation detection are contact hole patterns formed on the exposed layer (photoresist coating), are described below. In this case, although microstructured pattern images are acquired using a scanning-type electronic microscope, these pattern images can likewise be acquired using a means other than a scanning-type electronic microscope, such as an optical microscope.

First, in step 11, the microstructured pattern images that have been acquired using a means such as a scanning-type electronic microscope, are displayed on an image display unit and then an image of any single contact hole pattern is specified using a mouse cursor or the like. In step 12, polar coordinate conversions are performed on the selected contact hole pattern image, then a plurality of cross-sectional waveform information is created as profiles on a fixed-angle basis in a radial direction from the center of the contact hole pattern, and these profiles are provided with various differentiation processes and threshold value processes to derive several target edges. Among all these target edges, only the edge corresponding to the exposed layer surface of the contact hole pattern (hereinafter, this edge is called the inner circle) and the edge corresponding to the exposed layer bottom (hereinafter, this edge is called the outer circle) are detected. The further structural complexity and finesse of the microstructured patterns themselves, improvements in the performance of the inspection apparatus to be used, and other factors are offering a more abundance in terms of the edge information obtained as profiles, thereby making it more difficult to detect the edge corresponding to the desired position. The sections corresponding to the above-mentioned outer and inner circles (edges), however, are abundant in edge information and exist at almost a fixed distance in all angle directions from the center of the contact hole (namely, those sections take a circular shape). Therefore, the edge corresponding to the desired position can be detected more accurately by deriving as more target edges as possible and then detecting the outer and inner circles from edge information.

In step 13, the centers of gravity of the inner and outer circles that were detected in step 12 are derived as M1 and M2, respectively. In this step, although position information on the inner and outer circles is represented as the centers of gravity, the crossing point between the major and minor axes of a circle, for example, can also be taken as the position information relating to the circle. In this case, however, fixed criteria must always be used during a series of inspection processes for microstructured patterns. In step 14, the vector pointing from the gravity center M1 of the inner circle towards the gravity center M2 of the outer circle is calculated as the dislocation vector of the contact hole. Before this calculation is made, the tolerance for the dislocation of the microstructured patterns must be set through, for example, visually checking the image that was acquired by the inspection apparatus. The maximum and minimum allowable vectors should be established as the dislocation tolerance. Likewise, tolerances should also be set for the areas or major and minor diameters of the inner and outer circles, or for the area ratio between the circles. Thus, the calculated dislocation vector is judged whether it is out of the tolerance.

Figure 4:
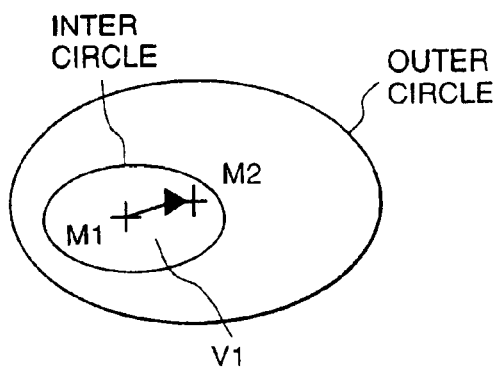
FIG. 4 is a diagram showing an example in which the inner and outer circles of a contact hole pattern and the corresponding dislocation vector are displayed on the screen.

As shown in FIG. 4, the inner and outer circles that have been measured at each angle with respect to the selected contact hole are displayed on the screen of the image display unit as the circles connecting the to-be-detected edges having the edge information corresponding to those measured circles, and as the arrow connecting the dislocation vector (calculated in step 14) from M1 towards M2. In FIG. 4, although the positive direction of the dislocation vector is shown as the direction from M1 to M2, the direction from M2 to M1 can also be set as the positive direction, only if fixed criteria is always used.

During the judgment process of step 14, if the size and direction of the dislocation vector fall within the previously set tolerance, processing will advance from step 14 to step 15 and the inner and outer circles of the contact hole and the dislocation vector will be displayed in white on the screen to indicate that the circles and the dislocation vector stay within their tolerances. Conversely, if the size and direction of the dislocation vector overstep the previously set tolerance, processing will skip to step 16 and the inner and outer circles of the contact hole and the dislocation vector will be displayed in red to warn the user that the circles and the dislocation vector are outside their tolerances.

Figure 5:
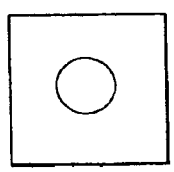
FIG. 5 is a diagram showing an example of categorizing on the shapes of contact hole patterns.
Figure 5:
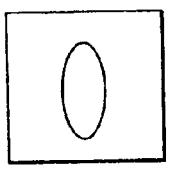
Figure 5:
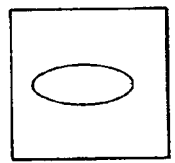
Figure 5:
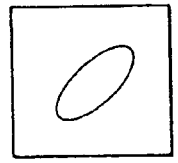
Figure 5:
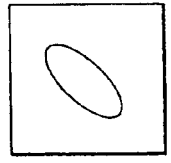
Figure 5:
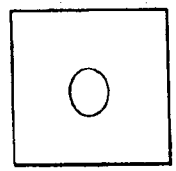
Figure 5:
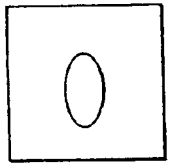
Figure 5:
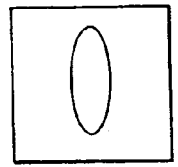
Figure 5:
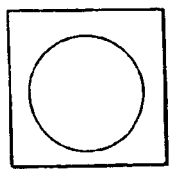
Figure 5:
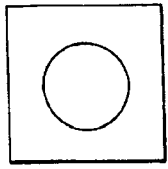
Figure 5:
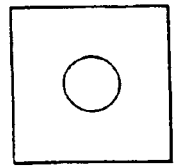

In addition to or instead of the dislocation vector, the shapes of the inner and outer circles of the contact hole should be used as a criterion for judging whether the particular contact hole is an allowable hole. Typical categories relating to the shapes of the inner and outer circles include, as shown in FIG. 5, the degree of circularity (whether the circle is a true circle or an ellipsis), the ratio of the major and minor diameters, the absolute area value, or the area ratio of the inner and outer circles. These shapes of the circles should be categorized either as large, medium, or small shapes, or according to the particular ratio relative to a reference value. At the same time, tolerances on individual categories should also be established. The shapes of the inner and outer circles of the contact hole to be inspected are compared with the respective tolerances after being analyzed whether the shapes belong to which of the established categories.

Figure 6:
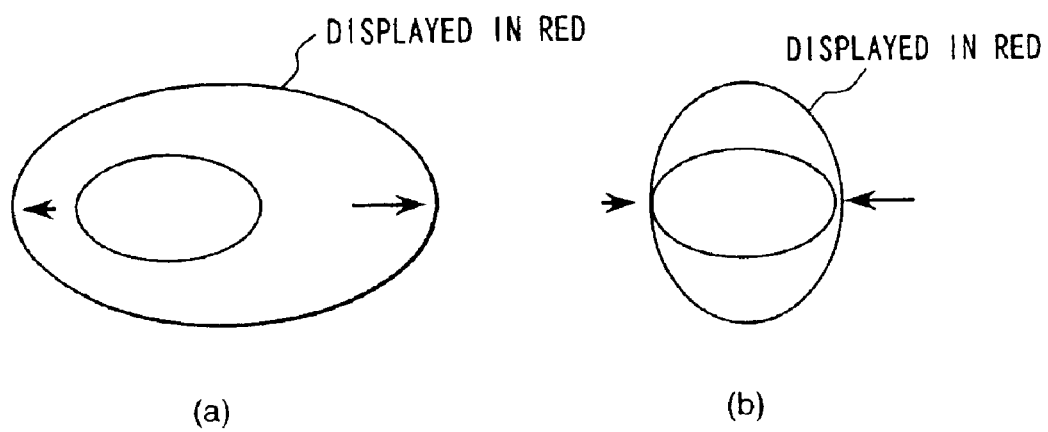
FIG. 6 is a diagram showing an example in which a warning will be displayed if the major and/or minor diameter or area of the inner and/or outer circle of a contact hole pattern oversteps the corresponding tolerance.
Figure 6:
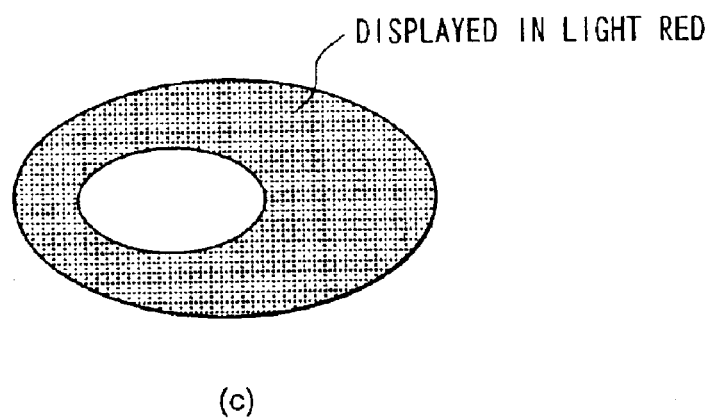

If the shape of the contact hole oversteps the tolerance, that contact hole will be displayed in color on the image display unit as a warning. FIG. 6 shows an example in which the shape of the contact hole will be displayed if the tolerance is overstepped. An example of the display made if the outer circle is greater than its maximum allowable major diameter is shown in FIG. 6 (a), wherein the difference from the tolerance is displayed as an arrow and the outer circle itself is displayed in a color meaning a warning, such as red. An example of the display made if the outer circle is smaller than its minimum allowable major diameter is shown in FIG. 6 (b), wherein the difference from the tolerance is displayed as an arrow and the circle corresponding to the outer circle is displayed in a color meaning a warning, such as red. An example of the display made if the outer circle is smaller than its minimum allowable area is shown in FIG. 6 (c), wherein the inside of the outer circle is displayed in a color meaning a warning, such as light red. Although the examples shown in FIG. 6 are for evaluating the shape of the outer circle of a contact hole, similar evaluations can also be performed on the inner circle of the contact hole.

Figure 7:
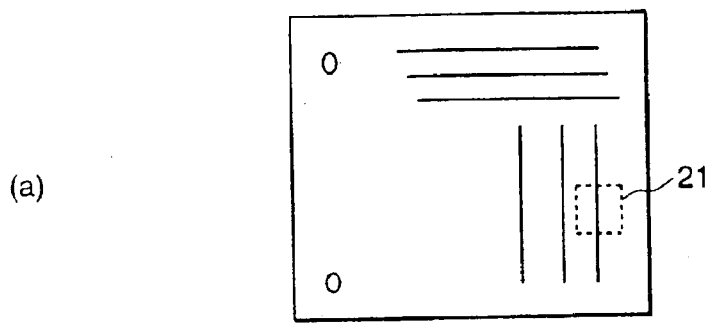
FIG. 7 is a diagram showing an example in which the exposed surface layer patterns, bottom layer patterns, and dislocation vectors of linear patterns are displayed on the screen.
Figure 7:
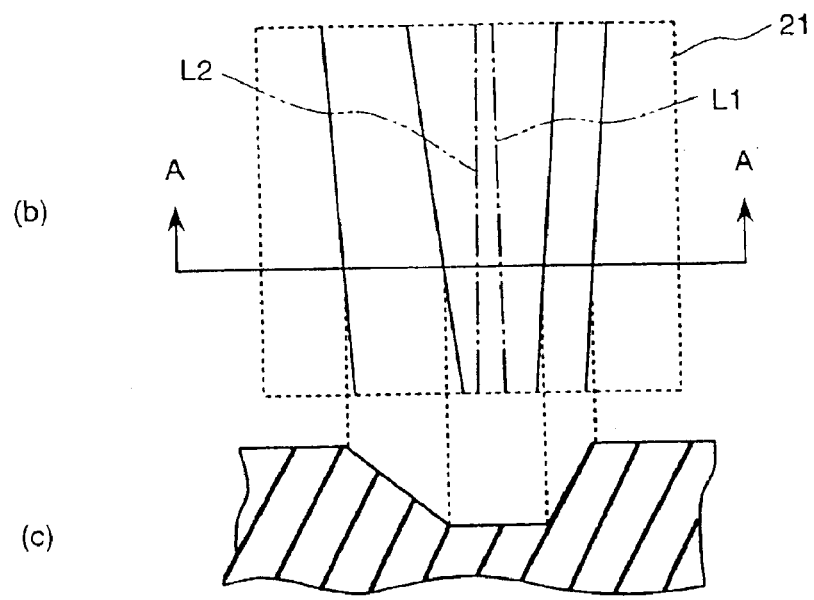
Figure 7:
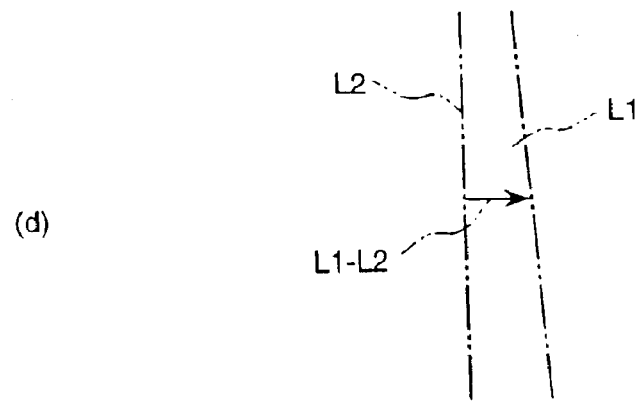

Next, the methods of detecting and displaying a dislocation vector in the case that the microstructured patterns to be inspected are linear patterns formed on exposed layers are described with reference being made to the flowcharts of FIGS. 3 and 7.

First, in step 11 of FIG. 3, images of the linear patterns to be inspected using a microstructured pattern inspection apparatus such as a scanning-type electronic microscope or optical microscope. Next, in step 12, fixed detection range 21 is set, as shown in FIG. 7 (a), for the acquired linear pattern images and then as shown in FIG. 7 (b), edges are detected within detection range 21, wherein the linear edges on the surface and at the bottom of the exposed layer (photoresist coating). After this, processing proceeds to step 13, in which the central axes of the linear edges on the surface and at the bottom of the photoresist coating are obtained as L1 and L2, respectively, as shown in FIG. 7 (b). FIG. 7 (c) is a cross-sectional view of section A—A shown in FIG. 7 (b). The perpendicular line from the center of axis L1 in detection range 21 to axis L2 is recognized as the dislocation vector (L1–L2) of the linear pattern as shown in FIG. 7 (d).

In this case as well, the tolerance for the dislocation is set through, for example, visual image checks using the inspection apparatus. In step 14, comparison is made between the dislocation vector that was calculated in step 13, and the dislocation tolerance that has been established beforehand. During the judgment process of step 14, if the size of the calculated dislocation vector falls within the previously set tolerance, processing will skip to step 16 and the edge and dislocation vector of the linear pattern will be displayed in red as a warning. Conversely, if the size of the dislocation vector oversteps the previously set tolerance, processing will advance to step 15 and the edge and dislocation vector of the linear pattern will be displayed in white on the screen.

Figure 8:
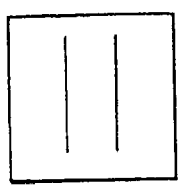
FIG. 8 is a diagram showing an example of categorizing the exposed surface layer patterns and bottom layer patterns of linear patterns.
Figure 8:
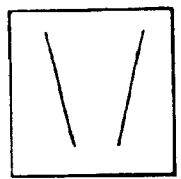
Figure 8:
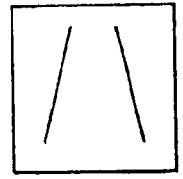
Figure 8:
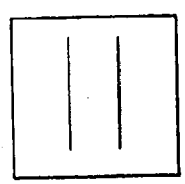
Figure 8:
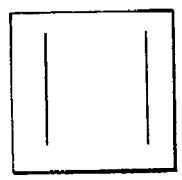
Figure 8:
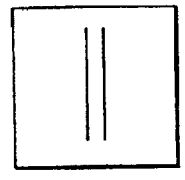

As with those of contact hole patterns, the shapes of linear patterns can be categorized separately for the surface and bottom each of the exposed layer (photoresist coating), and whether the particular linear pattern is an allowable pattern can be judged. Typical categories relating to the shapes of linear patterns include, as shown in FIG. 8, the shape, line width, etc. of the pattern. Tolerances should also be established for the shapes and widths of the linear patterns so that if a linear pattern oversteps the tolerances, that linear pattern will be displayed in a color, such as red, to warn the operator.

Next, the evaluation of a plurality of stepper-exposed contact hole and linear patterns or other microstructured patterns, especially, the method of evaluating an area equivalent to a single reticle shot or chip is described. An example of evaluating microstructured patterns using two indexes . . . dislocation vector and shape . . . is shown in this description.

Figure 9:
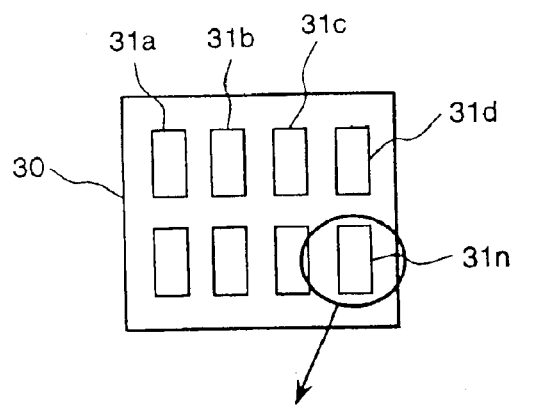
FIG. 9 is a diagram showing an example of selecting microstructured patterns as samples for calculating their dislocation vectors at each chip within a single-shot area.
Figure 9:
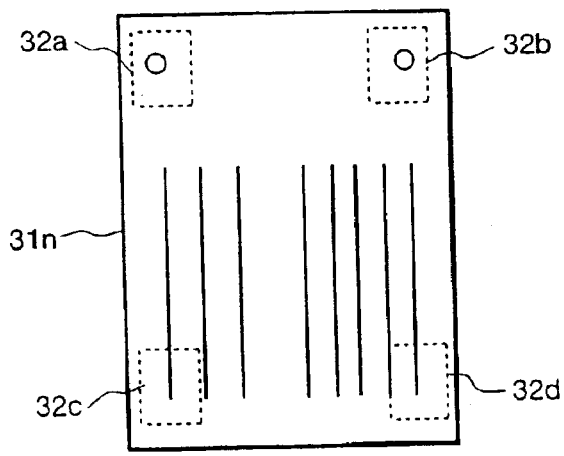

As shown in FIG. 9, multiple chips (31a, 31b, 31c, and so on) usually exist in single-shot area 30. First, a single shot of image information on exposed patterns is acquired by the scanning-type electronic microscope or other inspection apparatus. Contact hole patterns or linear patterns are selected at multiple positions within a single-shot area, then shape information is acquired for each pattern, and the dislocation vectors of each contact hole or linear pattern are calculated using the method described in the flowchart of FIG. 3. At this time, in chips 31a, 31b, 31c, and so on, of a single-shot area, sample patterns for calculating dislocation vectors at typical positions such as the corners (32a to 32d) and center (32e) of each chip, should be selected in order to implement chip comparison as well as shot comparison. Also, it is desirable that unless inspection throughput does not decrease significantly, more such sample patterns as possible should be selected at equal intervals within the chip area. In addition, these sample patterns should be acquired at the same position of each chip.

Figure 10:
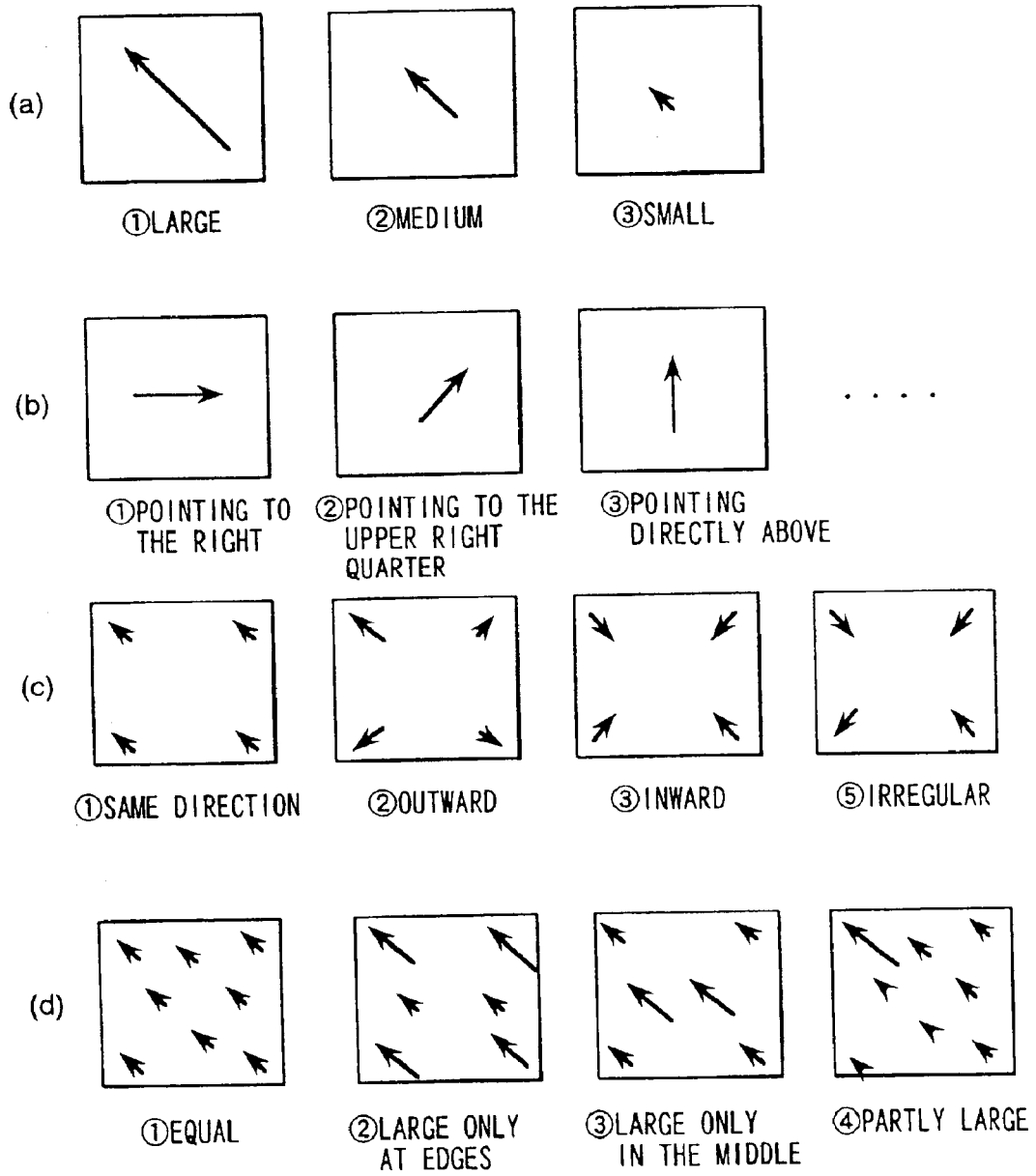
FIG. 10 is a diagram showing an example of categorizing the dislocation vectors that were derived from multiple positions.

The dislocation vectors that have been calculated for each contact hole pattern or linear pattern are displayed as arrows each originating from, for example, the gravity center position of the particular contact hole pattern or linear pattern. If the calculated dislocation vectors overstep the respective tolerances, a warning will be displayed in red. With respect to these calculated dislocation vectors at each sample within the single-shot or single-chip area, the corresponding patterns will then be categorized as shown in FIG. 10. For the entire single-shot area, the patterns will be categorized according to the size (large, medium, or small) of the entire dislocation vector shown in FIG. 10 (a), and according to the direction (either of about eight directions such as top, upper right, right, lower right, bottom, lower left, left, and upper left) of the entire dislocation vector shown in FIG. 10 (b).

The contact hole patterns or linear patterns are also categorized according to the particular direction and dimensional deviation of each dislocation vector that was acquired at a typical position within the single-shot or single-chip area. For direction, the dislocation vector at each sample is characterized, depending on, for example, as shown in FIG. 10 (c), whether the vector points in the same direction, outward, inward, or in an irregular direction. For dimensional deviations, individual dislocation vectors are characterized, depending on, for example, as shown in FIG. 10 (d), whether the patterns are equal, large only at edges, large only in the center of the reticle, or large in a specific position only. Each characteristic quantity is linked to the area from which the particular characteristics have been extracted. The methods of categorizing patterns are not limited to the four types shown in FIG. 10; other characteristic quantities can be used instead, provided that they represent the tendencies of the dislocation vectors within the single-shot area.

The dislocation vectors representing the entire single-shot or single-chip area are calculated as follows:

In the "k"th area of chips, for example, a contact hole pattern of one "k" chip and a linear pattern of two "k" chips are set as sample patterns for the calculation of the corresponding dislocation vectors, and each chip is provided with such processing as described in the flowchart of FIG. 3. When the dislocation vectors that have thus been calculated for the contact hole pattern are taken as $SH_1$, $SH_2$, and so on up to $SH_{k1}$, and the calculated dislocation vectors of the linear pattern are taken as $SL_1$, $SL_2$, and so on up to $SL_{k2}$, dislocation vector $VC_k$ representing the chip can be calculated using expression 1 below. If each pattern differs in design specifications, since the sizes of the dislocation vectors calculated will also differ, adjustments will be performed using coefficients α and β. The dislocation vectors representing each shot area can also be calculated similarly.

$$\vec{VC_k} = \sum_{i=1}^{k1} \alpha_i \vec{SH_i} + \sum_{j=1}^{k2} \beta_j \vec{SL_i}$$ [Expression 1]

After the contact hole and linear patterns have been categorized by their shapes as shown in FIG. 5 or 6, the results are statistically processed in the single-shot or single-chip range, and for example, the largest value in terms of the number of categories is taken as a typical value of the shape relating to the corresponding area.

The occurrence of some abnormality caused by the four factors described earlier in this SPECIFICATION can be estimated by characterization relating to the thus-calculated sizes and distributions of the dislocation vectors within a single-shot area, and from categorizing results on the shapes of the contact hole or linear patterns.

Figure 11:
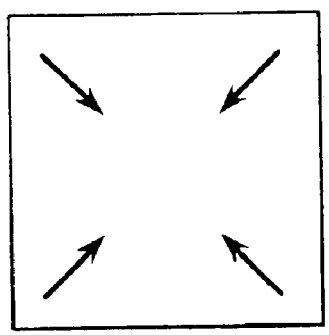
FIG. 11 is a diagram showing the tendency of microstructured pattern dislocations due to lens aberration, and the tendency of microstructured pattern deformation.
Figure 11:
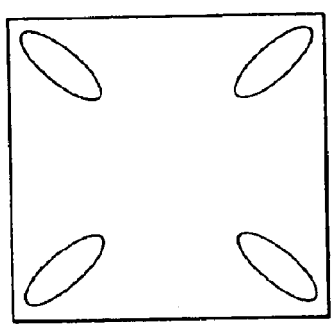
Figure 11:
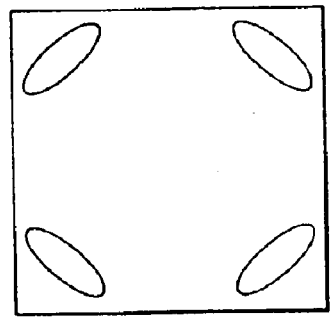

FIG. 11 shows the tendency of dislocation vectors occurring in a single-shot area when lens aberration is detected in the pattern projection optics. For example, if, as shown in FIG. 11 (a), the dislocation vector points in a radially inward direction from the center of the reticle within a single-shot area, or if the contact hole is deformed into either a vertically long shape towards the center of the reticle as shown in FIG. 11 (b), or a horizontally long shape towards the center of the reticle as shown in FIG. 11 (c), such abnormality is likely to be due to lens aberration in the stepper. If these characteristics are detected, therefore, a warning implying the occurrence of lens aberration in the projection optics of the stepper will be displayed along with images of the corresponding pattern.

Figure 12:
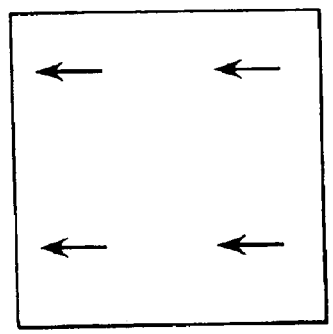
FIG. 12 is a diagram showing the tendency of a dislocation occurring if the projection optics is axially misaligned or has any inclined lenses.

FIG. 12 shows the tendency of dislocation vectors occurring when the projection optics is axially misaligned or has any inclined lenses. If, as shown in FIG. 12, multiple dislocation vectors within a single-shot area point in the same direction, this implies abnormality due to axial misalignment of the projection optics. If these characteristics are detected, therefore, a warning will be issued by, for example, displaying a message indicating the abnormality.

Figure 13:
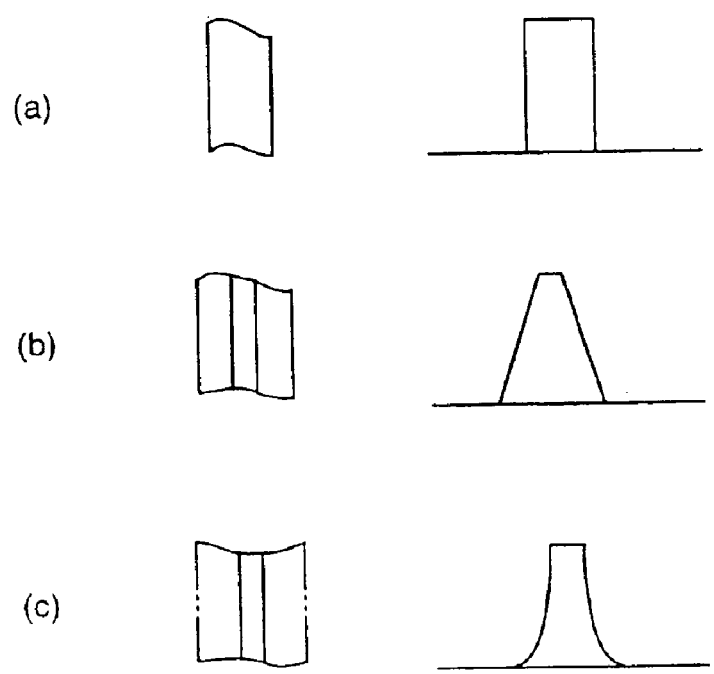
FIG. 13 is an explanatory diagram of the linear patterns formed when defocusing due to lens heating is occurring.

FIG. 13 is an explanatory diagram of the linear patterns formed when defocusing due to lens heating is occurring. The linear pattern formed when the best focus is obtained, is shown in FIG. 13. (a), and the linear patterns formed during defocusing are shown in FIGS. 13 (b) and (c). Shown at the left of FIGS. 13 (a), (b), (c) each are top views of the linear pattern, and shown at right are cross-sectional epitomic views of the linear pattern. FIG. 13 (b) shows a linear pattern whose defocusing direction is plus (this indicates that the focal position is above the exposed surface), and this linear pattern has a thin top and is thicker as it goes downward. FIG. 13 (c) shows a linear pattern whose defocusing direction is minus (this indicates that the focal position is below the exposed surface), and this linear pattern has a thin top and a flared, indistinct bottom. Since these patterns having a thin top and/or a thick/indistinct bottom are likely to be due to defocusing, a warning is displayed to imply the occurrence of the abnormality. Lens heating is caused by the accumulation of heat inside, and on the surfaces of the lenses due to continued exposure for a long time. Characteristics on the "lens heating" event of the lenses to be used can be understood by examining chronological changes in the shape of the pattern.

Figure 14:
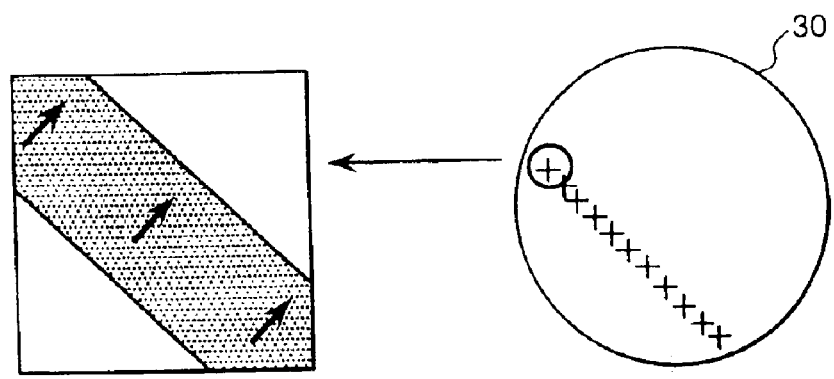
FIG. 14 shows an example of a tendency occurring with the dislocation vectors if the wafer itself is deformed or if the photoresist coating is not uniform.

FIG. 14 shows an example of a tendency occurring with the dislocation vectors if the wafer itself is deformed or if the photoresist coating is not uniform. Warped or deflected wafer or nonuniform photoresist coating affects the axial misalignment of the entire wafer significantly. Factors due to defects in wafer status, however, can be evaluated by calculating dislocation vectors with respect to each chip within each wafer and examining their tendencies. As briefly shown in FIG. 14, abnormality due to either defects in the status of the wafer itself or nonuniform photoresist coating, is usually distributed in one specific area of wafer 30. Therefore, the occurrence of abnormality due to either defects in the status of the wafer itself or nonuniform photoresist coating, can be estimated by concentrating attention on such specific characteristics and analyzing their distributions within the wafer area.

The method of displaying information on the dislocation vectors and shapes of microstructured patterns such as contact hole and linear patterns, is described next. One or more areas are specified for each chip in each wafer area, and any dislocation vectors in the specified area(s) are calculated. Also, dislocation vectors for each chip or each shot are characterized using a similar method to [Expression 1] shown above. When information on the dislocations of microstructured patterns is displayed, either a view showing the wafer when it is partitioned into shot areas, or a view showing a specific shot area when it is partitioned into chip areas is displayed on the screen of the display unit first and then the dislocation vectors that were calculated for each shot area of the wafer or for each chip area in a specific shot are displayed in color. As with the processing sequence shown in the flowchart of FIG. 3, if the dislocation vectors overstep the respective tolerances for each shot or each chip, a warning will be issued by displaying the vectors in a conspicuous color such as red.

Figure 15:
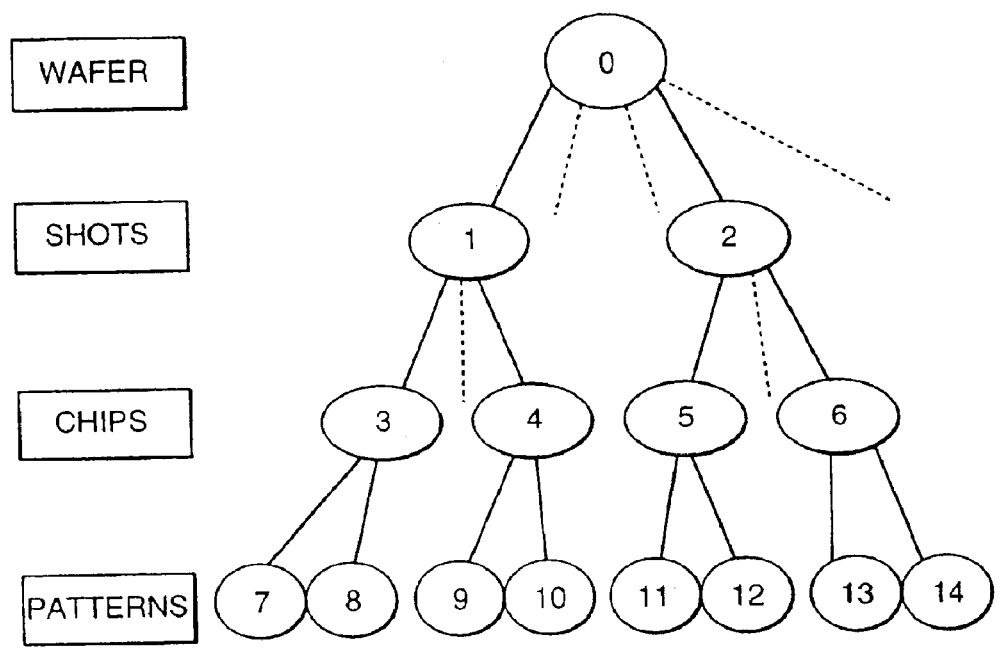
FIG. 15 is an explanatory diagram of the database structure of the dislocation vector and characteristic quantity data calculations obtained from each pattern of a wafer.

FIG. 15 is an explanatory diagram of the saving format of the dislocation vector and characteristic quantity data calculations obtained from each pattern of a wafer. The data is of the tree structure having a hierarchy covering the wafer, shots, chips, and in-chip patterns. Each in-chip pattern record has pattern's x- and y-coordinates, pattern information (whether the pattern has a linear shape or a contact hole shape), the size and direction of the dislocation vector of the corresponding pattern, shape information, and other characteristic quantities. On a chip-by-chip basis, the average of various information on the pattern belonging to the chip is retained as a record of that chip. Likewise, on a shot-by-shot basis, the average of various information on the chip corresponding to the shot is retained as a record. Also, each value retains as its "parent" the ID of the area of the immediately upper hierarchical level, as its "brother" the ID of an area derived from that parent, and as its "child" the ID of the immediately lower hierarchical level of direct lineage. Chip "3", for example, retains "1" as its parent, "4" as its brother, and "7" and "8" as its children.

Figure 16:
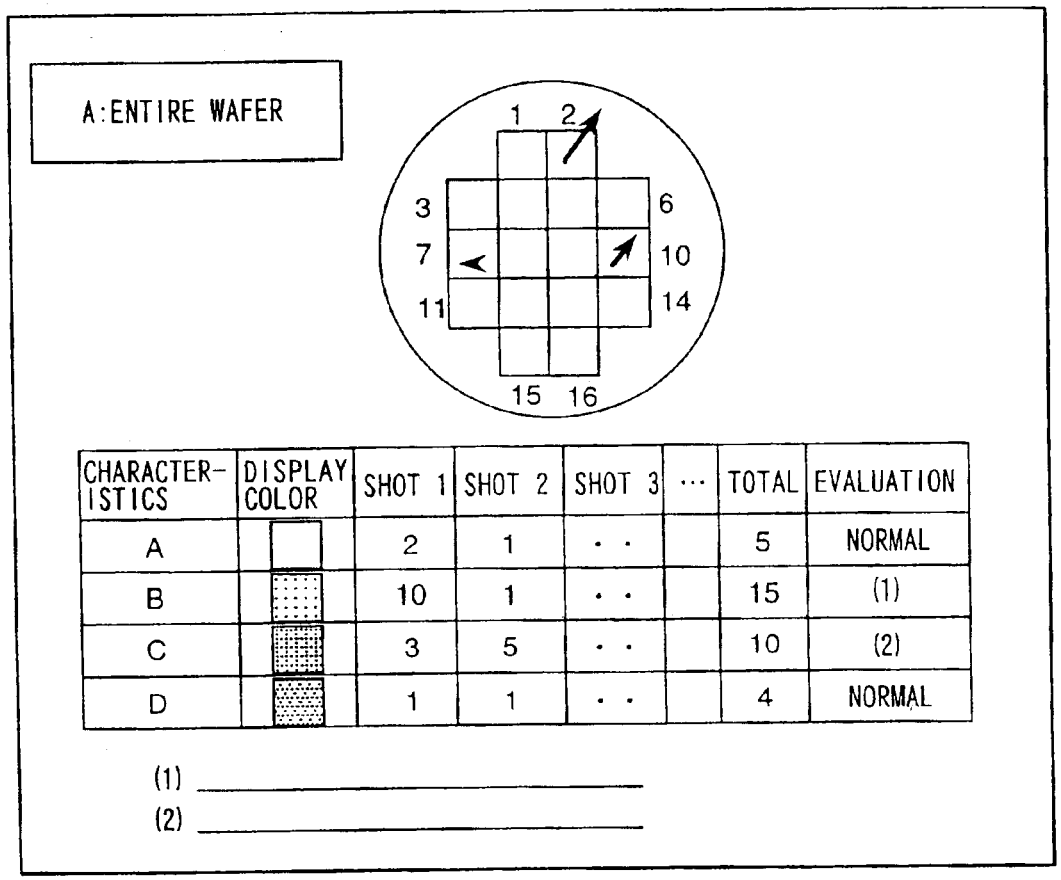
FIG. 16 is a diagram showing an example of a screen display made for the evaluation of dislocation vectors and characteristic quantities on a wafer-by-wafer basis.
Figure 17:
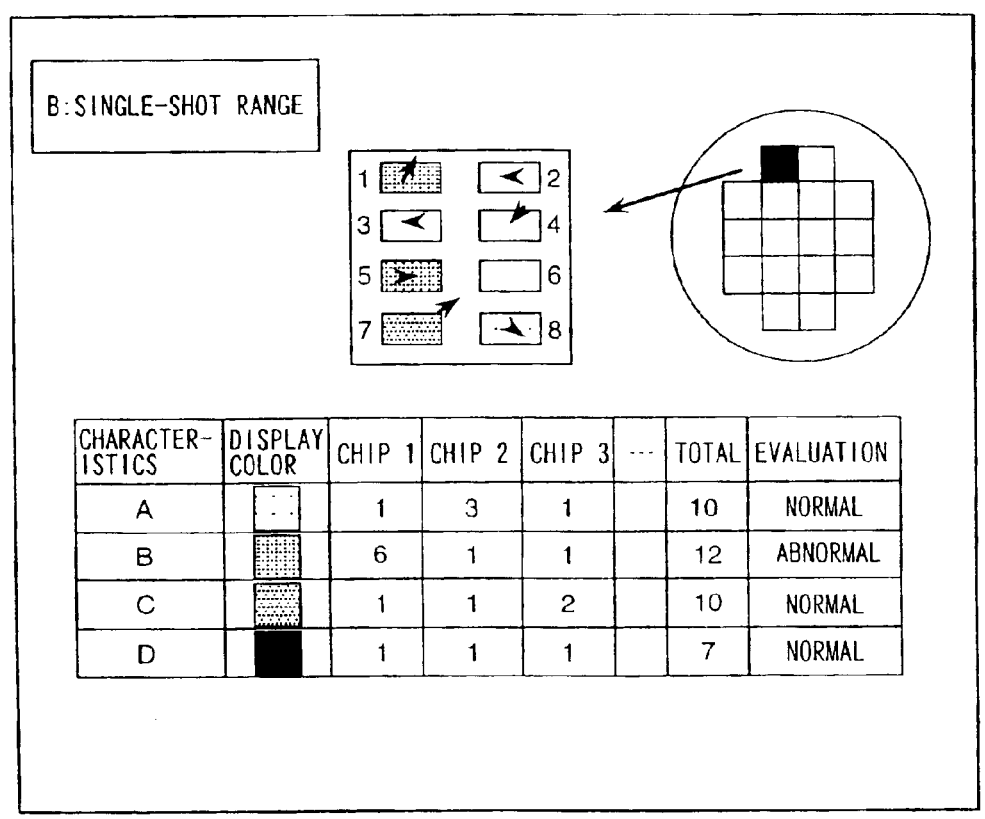
FIG. 17 is a diagram showing an example of a screen display made for the evaluation of dislocation vectors and characteristic quantities on a single-shot basis.

Examples in which the dislocation vector characteristic quantities that have been acquired using the method described above are statistically processed and displayed on the screen, are shown in FIGS. 16 and 17. The display shown in FIG. 16 relates to the corresponding wafer, and the display in FIG. 17 is for the corresponding shot range.

As shown in FIG. 16, wafer display mode displays information on a shot-by-shot basis. On the wafer map, each shot area is partitioned by a shape such as a square, and the characteristic quantity and dislocation vector of each entire shot area are displayed. A specific number from 1 to 16 is assigned to each shot area, with the number corresponding to the coordinates within the wafer. Each shot area from 1 to 16 on the wafer map is displayed properly in color coded form according to the characteristic quantity representing the shot (the greatest characteristic quantity in the shot: A, B, C, or, D). Also, the dislocation vector representing the shot area is displayed in overlapped form on that shot area. The distribution of characteristic quantities on the shape of the microstructured pattern is digitally displayed in the table at the bottom of the display. Numerals in this table denote the number of times each characteristic quantity appeared in each shot area. At the right end of the table is displayed the total number of times each characteristic quantity appeared in the entire shot range, and if this appearance tendency shows any characteristics, these characteristics will be displayed under "Evaluation". When a typical tendency is analyzed beforehand and actual evaluations apply to that tendency, explanatory statements on further detailed analyses on the tendency will be displayed with "(1)" or "(2)" at the bottom of the screen display.

As shown in FIG. 17, chip display mode displays information on a chip-by-chip basis. In shot display mode, a map of the wafer is also displayed at the same time to indicate to what position on the wafer map the current shot corresponds. Each chip from 1 to 8 within the shot is displayed properly in color coded form according to the characteristic quantity representing the chip (the greatest characteristic quantity in the chip: A, B, C, or, D). Also, the dislocation vector representing the chip is displayed in overlapped form on that chip. The distribution of characteristic quantities on the shape of the microstructured pattern is digitally displayed in the table at the bottom of the display. At the right end of the table is displayed the total number of times each characteristic quantity appeared, and if this appearance tendency shows any characteristics, these characteristics will be displayed under "Evaluation". When a typical tendency is analyzed beforehand and actual evaluations apply to that tendency, explanatory statements on further detailed analyses on the tendency will be displayed with "(1)" or "(2)" at the bottom of the screen display. In the example of FIG. 17, "Abnormal" is shown as the evaluation of characteristic quantity B, and the column of chip 1 is displayed in light red.

The display shown in FIG. 16 or 17 changes according to the characteristic quantity to which attention is to be given (the layout of the display remains the same). For example, if this characteristic quantity is "A: Characteristics of the circle" as shown at the top of FIG. 5, the characters "True circle", "Vertically long", "Horizontally long", "Oblique (1)", and "Oblique (2)", are assigned to the items of characteristic quantities A, B, C, D, and E, respectively, in FIG. 16 or 17. When five categories are present, the number of items is also five (from A to E) and five different colors are assigned as display colors. The display of each shot or chip area is coded in the color corresponding to the characteristic quantity representing the area. Also, "Characteristic quantity" in the table functions as a button, and with each press of this button, the categorizing basis in FIG. 5 changes to "Characteristics of the circle" first and then "Ellipticity", "Area", and so on, in that order. As "Characteristic quantity" changes in this way, the numeric data in the table and the display color of the shot area within the wafer map or of the chip area within the shot will also correspondingly change.

Although it is not shown in the corresponding FIG., display mode for a single-chip range is also provided. This display mode for a single-chip range is very similar to the display mode for a single-shot range, and in the single-chip display mode, any dislocation vectors of the sample patterns within one chip are displayed at the patterns. The shot display also appears at the same time so that the position of the current chip in the shot can be readily identified.

Figure 18:
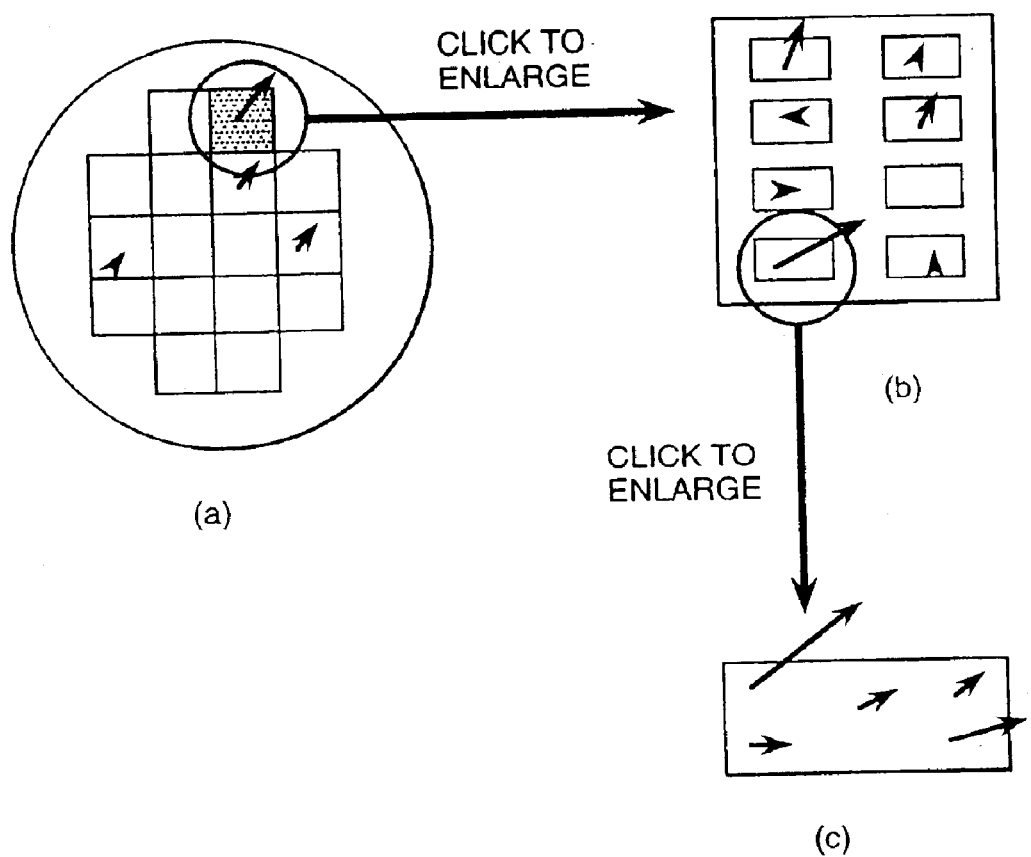
FIG. 18 is a diagram representing the relationship between wafer display, shot display, and chip display.

FIG. 18 shows the relationship between wafer display, shot display, and chip display. In the wafer display mode shown in FIG. 18 (a), for example, if the operator clicks in shot area 2 on the display with a large dislocation vector, the current display will change to the shot display mode to display that shot in enlarged form as shown in FIG. 18 (b). Average dislocation vectors on each chip of the shot are displayed in the shot display mode, and in this mode, if the operator clicks at chip 7 on the display with a large dislocation vector, that chip will be displayed in enlarged form and the distribution of dislocation vectors in the chip will also be displayed, as shown in FIG. 18 (c). Thus, the position with a significant dislocation vector can be detected. It is also possible to move control to the shot display mode by double-clicking on the shot display, and to return control to the original shot display mode by double-clicking on the chip display. The database structure shown in FIG. 15 is used during movement from the wafer display mode to the shot display mode, or vice versa. For example, when control is moved from the display of shot 1 to that of a chip, the corresponding chip display is created using the information of chips 3 and 4.

FIG. 19 is a flowchart explaining the entire procedure relating to microstructured pattern inspection based on the present invention. First, in step 21, the wafer to be inspected is loaded into an inspection apparatus such as a scanning-type electronic microscope or optical microscope. Next, in step 22, the shot (or chip) to be inspected for dislocation vector or geometrical characteristics of the microstructured pattern is specified, and processing further advances to step 23, wherein the dislocation vector calculating position in the shot (or chip) is then specified.

Next, in steps 24 to 28, dislocation vector calculation and characterization are executed for the specified microstructured pattern. In step 29, the calculated dislocation vector or the characteristic quantity of shape is judged whether the corresponding tolerance is overstepped, and if the tolerance is not overstepped, processing will proceed to step 30, wherein the dislocation vector or the microstructured pattern will then be displayed in normal color. Conversely, if the tolerance is overstepped, processing will skip to step 31, wherein the dislocation vector or the microstructured pattern will then be displayed in red as a warning.

Processing will proceed to step 32, wherein characteristic tendencies on either the distribution of the dislocation vectors that were calculated in steps 24 to 28, or the shape of the specified microstructured pattern will then be statistically analyzed. Processing will further proceed to step 33, wherein judgment will be made whether the tendency of characteristic quantities that was analyzed in step 32 will imply abnormality about the stepper or wafer. In the judgment process of step 33, a combination of, for example, such dislocation vector distribution patterns as shown in FIGS. 11 (a), 12, and 14, and the known causes of the abnormality, or a combination of such pattern shape-related characteristic quantity distribution patterns as shown in FIGS. 11 (b), 11 (c), and 13, and the known causes of the abnormality, is retained as a table, and the tendency of the characteristic quantities that were calculated in step 32 is checked against the table to search for the actual cause of the abnormality. If the distribution pattern of the dislocation vectors or the distribution of the shape-related characteristic quantities of the microstructured pattern exists in the table and implies abnormality about the stepper or wafer, processing will advance to step 34 and a warning message on the cause of the abnormality will be displayed.

According to the present invention, microstructured pattern exposure accuracy can be automatically evaluated and easily confirmed. Also, trouble in the optics of the stepper or in the wafer can be detected by evaluating the distributions of the characteristics of microstructured patterns over a broader area such as a single-chip or single-shot area or the entire wafer.

What is claimed:

1. A pattern inspection method for inspecting a pattern formed in a chip of a semiconductor wafer containing a plurality of chips, comprising: forming a pattern image of each chip of the semiconductor wafer, or of an area shot by an optical exposure apparatus, on the semiconductor wafer, with a scanning electron microscope;
   detecting a deviation between a surface and a bottom of a pattern for each chip or for the area shot by the optical exposure apparatus based on the image; and
   displaying information regarding the deviation between the surface an the bottom, for each chip or area shot by the optical exposure apparatus, on a wafer map.

2. A pattern inspection method according to claim 1, wherein the pattern is a line pattern and/or a hole pattern.

3. A pattern inspection method according to claim 1, wherein the deviation is a difference between the centers of gravity of the surface and the bottom of at least one hole pattern on the semiconductor wafer.

4. A pattern inspection method according to claim 1, wherein the deviation is a difference between two central axes of the surface and the bottom of at least one line pattern.

5. A pattern inspection method according to claim 1, wherein deviations are determined for a plurality of patterns on each chip or area shot by the optical exposure apparatus and the information displayed is calculated by taking a statistic of the deviations for each chip or area shot by the optical exposure apparatus.

6. A pattern inspection method according to claim 1, wherein deviations are determined for a plurality of patterns on each chip or area shot by the optical exposure apparatus and the information displayed is a typical value of the deviation for each chip or area shot by the optical exposure apparatus.

7. A pattern inspection method according to claim 1, wherein the information is displayed with a plurality of different colors respectively representing different magnitudes of the deviations.

8. A pattern inspection method for inspecting patterns formed in chips of a semiconductor wafer, comprising: forming a pattern image of each chip of the semiconductor wafer or of an area shot by an optical exposure apparatus on the semiconductor wafer with a scanning electron microscope; detecting deviations between surfaces and bottoms of patterns for each chip or for the area shot by the optical exposure apparatus based on the images; and calculating a characteristic magnitude of the deviations for each chip, for the area shot by the optical exposure apparatus, or for the semiconductor wafer.

9. A pattern inspection method according to claim 8, further comprising: displaying the characteristic magnitude for each chip, for the area shot by the optical exposure apparatus, or for the semiconductor wafer.

10. A pattern inspection method according to claim 8, wherein the patterns are line patterns and/or hole patterns.

11. A pattern inspection method according to claim 8, wherein the deviations are differences between centers of gravity of the surface and the bottom of hole patterns on the semiconductor wafer.

12. A pattern inspection method according to claim 8, wherein the deviations are differences between two central axes of the surface and the bottom of line patterns.

13. A pattern inspection method according to claim 8, wherein the characteristic quantity is calculated by taking a statistic of a plurality of deviations for each chip, for the area shot by the optical exposure apparatus, or for the semiconductor wafer.

14. A pattern inspection method according to claim 8, wherein the characteristic magnitude is a typical value of the deviations for each chip, for the area shot by the optical exposure apparatus, or for the semiconductor wafer.

15. A pattern inspection apparatus for inspecting a semiconductor wafer having a plurality of patterns on a plurality of chips, the apparatus comprising:
   an electron gun for obtaining an electron beam,
   a deflector for scanning the electron beam on the semiconductor device,
   a detector for detecting secondary electrons generated from the semiconductor wafer, and
   a display for displaying information regarding the patterns based on the detected secondary electrons, wherein
   the display displays deviation information regarding at least a deviation between a surface and a bottom of one pattern, for each chip or for an area shot by an optical exposure apparatus, as a wafer map.

16. A pattern inspection apparatus according to claim 15, wherein the display displays a deviation calculated by taking a statistic of a plurality of deviations, for each chip or for the area shot by the optical exposure apparatus.

17. A pattern inspection apparatus according to claim 15, wherein the display displays a typical value of the deviations for each chip or for the area shot by the optical exposure apparatus.

18. A pattern inspection method according to claim 15, wherein the display displays the deviations with a plurality of different colors, each representing a different magnitude of deviation.

19. A pattern inspection apparatus for inspecting a semiconductor wafer having a plurality of patterns on a plurality of chips, the apparatus comprising:
   an electron gun for obtaining an electron beam,
   a deflector for scanning the electron beam on the semiconductor device,
   a detector for detecting secondary electrons generated in the semiconductor wafer, and
   a display for displaying information about the patterns based on the detected secondary electrons,
   wherein the display displays a characteristic magnitude of deviations between a surface and a bottom of the patterns, calculated for each chip, for an area shot by an optical exposure apparatus, or for the semiconductor wafer.

20. A pattern inspection apparatus according to claim 19, wherein the display displays a characteristic magnitude for each chip, for the area shot by the optical exposure apparatus, or for the semiconductor wafer.

21. A pattern inspection apparatus according to claim 19, wherein the display displays a characteristic magnitude which is calculated by taking a statistic of a plurality of deviations for each chip, for the area shot by the optical exposure apparatus, or for the semiconductor wafer.

22. A pattern inspection apparatus according to claim 19, wherein the display displays a characteristic magnitude which is a typical value of the deviations for each chip, for the area shot by the optical exposure apparatus, or for the semiconductor wafer.

23. A pattern inspection apparatus for inspecting a semiconductor wafer having a plurality of patterns on a plurality of chips, the apparatus comprising:
   an electron gun for obtaining an electron beam,
   a deflector for scanning the electron beam on the semiconductor device,
   a detector for detecting secondary electrons generated from the semiconductor wafer,
   a display for displaying information about the patterns based on the detected secondary electrons, and
   a processor programmed to calculate deviation information regarding at least a deviation between a surface and a bottom of at least one pattern for each chip or an area shot by an optical exposure apparatus, the display displaying the deviation information as a wafer map.

24. A pattern inspection apparatus according t claim 23, wherein the processor calculates the deviation by taking statistic of the plurality of deviations for each chip or for the area shot by the optical exposure apparatus.

25. A pattern inspection apparatus according to claim 23, wherein the processor calculates a typical value of the deviations for each chip or for the area shot by the optical exposure apparatus.

26. A pattern inspection method according to claim 23, wherein the display displays the deviations with a plurality of different colors, each representative of a different magnitude of the deviation.

27. A pattern inspection apparatus for inspecting a semiconductor wafer having a plurality of patterns on a plurality of chips, the apparatus comprising:
   an electron gun for obtaining an electron beam,
   a deflector for scanning the electron beam on the semiconductor device,
   a detector for detecting secondary electrons generated in the semiconductor wafer, and
   a processor programmed to calculate deviation information regarding deviation between a surface and a bottom of at least one pattern for each chip or for an area shot by an optical exposure apparatus.

28. A pattern inspection apparatus according to claim 27, further comprising a display displaying said calculated deviation information for each chip, for the area shot by the optical exposure apparatus, or for the semiconductor wafer.

29. A pattern inspection apparatus according to claim 27, further comprising a display displaying a characteristic magnitude for each chip, for the area shot by the optical exposure apparatus, or for the semiconductor wafer.

30. A pattern inspection apparatus according to claim 27, further comprising a display displaying a characteristic magnitude which is calculate by taking a statistic of a plurality of deviations for each chip, for the area shot by the optical exposure apparatus, or for the semiconductor wafer.

31. A pattern inspection apparatus according to claim 27, further comprising a display displaying a characteristic magnitude which is a typical value of the deviations for each chip, for the area shot by the optical exposure apparatus, or for the semiconductor wafer.

* * * * *